(12) United States Patent
Kwon

(10) Patent No.: US 7,897,104 B2
(45) Date of Patent: Mar. 1, 2011

(54) STERILIZING CONTROL METHOD FOR DISHWASHER

(75) Inventor: Soon Yong Kwon, Busan (KR)

(73) Assignee: LG Electronics Inc., Seoul (KR)

( * ) Notice: Subject to any disclaimer, the term of this patent is extended or adjusted under 35 U.S.C. 154(b) by 395 days.

(21) Appl. No.: 11/798,445

(22) Filed: May 14, 2007

(65) Prior Publication Data

US 2007/0274856 A1 Nov. 29, 2007

(30) Foreign Application Priority Data

May 15, 2006 (KR) ...................... 10-2006-0043263

(51) Int. Cl.
*A61L 2/00* (2006.01)
*B08B 3/00* (2006.01)
(52) U.S. Cl. ............................ 422/1; 422/24; 134/58 D
(58) Field of Classification Search ..................... 422/4; 134/58 D
See application file for complete search history.

(56) References Cited

U.S. PATENT DOCUMENTS

| 3,571,939 | A | | 3/1971 | Paul |
| 3,915,180 | A | | 10/1975 | Jacobs |
| 5,603,776 | A | * | 2/1997 | Lentsch et al. ............. 134/25.2 |
| 6,578,586 | B2 | * | 6/2003 | Moh ......................... 134/25.2 |
| 2003/0150475 | A1 | * | 8/2003 | Abrams et al. ................. 134/1 |
| 2005/0150528 | A1 | * | 7/2005 | Kim ........................... 134/108 |

FOREIGN PATENT DOCUMENTS

EP 1550396 A2 7/2005

* cited by examiner

*Primary Examiner*—Sean E Conley
*Assistant Examiner*—Kevin C Joyner
(74) *Attorney, Agent, or Firm*—Birch, Stewart, Kolasch & Birch, LLP

(57) ABSTRACT

Provided is a sterilizing control method for a dishwasher. The method includes inputting a command for a sterilizing cycle, and turning a sterilizer disposed within a tub on and off at regular, predetermined intervals, according to the inputted command.

6 Claims, 4 Drawing Sheets

STERILIZING CONTROL METHOD FOR DISHWASHER

BACKGROUND OF THE INVENTION

1. Field of the Invention

The present invention relates to a dishwasher, and more particularly, to a sterilizing control method for a dishwasher for eradicating germs that breed inside the tub of a dishwasher after completion of a dishwashing course.

2. Description of the Related Art

Generally, a dishwasher is an apparatus that sprays washing water at high pressure within a tub to contact surfaces of dishes and wash away food residue and other impurities from the surfaces of the dishes.

Specifically, a dishwasher includes a tub forming a wash compartment, and a sump for storing washing water that is installed at the bottom of the tub. A wash pump installed in the sump prompts a flow of washing water to spray nozzles/arms, and the washing water that flows to the spray nozzles/arms is sprayed at high pressure through spray holes defined at the end portions of the spray nozzles/arms.

The washing water sprayed at high pressure collides against the surfaces of dishes, so that food residue and other impurities on the dishes fall to the floor of the tub.

A dishwasher according to the related art is capable of performing a pre-wash cycle, a main wash cycle, a rinse cycle, and a drying cycle (which are usually performed in said sequence). The main objective of such dishwashers is washing and drying dishes as thoroughly as possible.

However, there are often cases where condensed water collects within the tub after completion of the drying cycle, or moisture is not completely removed from the surfaces of dishes. In other words, the inside of the tub may not be dried completely, and thus retains a certain amount of moisture.

Dishwashers with built-in sterilizers, for preventing germ propagation within the tub, are now being launched in the consumer market.

In the case of such dishwashers according to the related art, however, the sterilizer performs only one sterilizing cycle of a predetermined duration after the drying cycle is completed. This sole sterilizing cycle is most often insufficient to eradicate germs.

Also, because germs that are not killed during the sterilizing cycle are able to proliferate at a higher rate, the sterilizing ability of the dishwasher is substantially compromised.

Furthermore, because the duration of a sterilizing cycle in a dishwasher according to the related art is too brief for completely eradicating germs, the sterilizing ability of the dishwasher is reduced.

SUMMARY OF THE INVENTION

Accordingly, the present invention is directed to a sterilizing control method for a dishwasher that substantially obviates one or more problems due to limitations and disadvantages of the related art.

An object of the present invention is to provide a sterilizing control method for a dishwasher that enables a plurality of sterilizing cycles to be performed at regular intervals to prevent germ propagation inside the tub of a dishwasher.

Another object of the present invention is to provide a sterilizing control method capable of performing only a sterilizing cycle, or adding a sterilizing cycle to other cycles in a dishwashing course when setting wash options at the onset of a wash course.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, there is provided a sterilizing control method for a dishwasher, including: inputting a command for a sterilizing cycle; and turning a sterilizer disposed within a tub on and off at regular, predetermined intervals, according to the inputted command.

In another aspect of the present invention, there is provided a sterilizing control method for a dishwasher, including: inputting wash preferences for a sterilizing cycle through a control panel; determining whether the inputted wash preferences are for performing a stand-alone sterilizing cycle, and turning a sterilizer on and off at regular intervals within a wash course or in a stand-alone sterilizing cycle; and ending the sterilizing cycle when an operating duration of the sterilizer reaches a set duration.

In a further aspect of the present invention, there is provided a sterilizing control method for a dishwasher, including: inputting wash settings through a control panel, for performing a stand-alone sterilizing cycle; operating a sterilizer for a set duration; turning the sterilizer off and operating a fan motor; and repeating the operating of the sterilizer and the fan motor, and ending the sterilizing cycle when a number of operations of the sterilizer reaches a set number.

The sterilizing control method for a dishwasher according to the present invention has the advantage of being able to completely eradicate pathogenic bacteria inside a tub, such as salmonella, vibrio, bacillus subtilis, etc.

Also, by repeatedly performing a sterilizing process at predetermined, regular intervals, the sustenance and propagation of bacteria can be stopped at the source.

Accordingly, the survival and re-growth of bacteria can be prevented in order to maintain a hygienic interior of a dishwasher.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DETAILED DESCRIPTION OF THE INVENTION

Reference will now be made in detail to the preferred embodiments of the present invention, examples of which are illustrated in the accompanying drawings. The invention may, however, be embodied in many different forms and should not be construed as being limited to the embodiments set forth herein.

Figure 1:
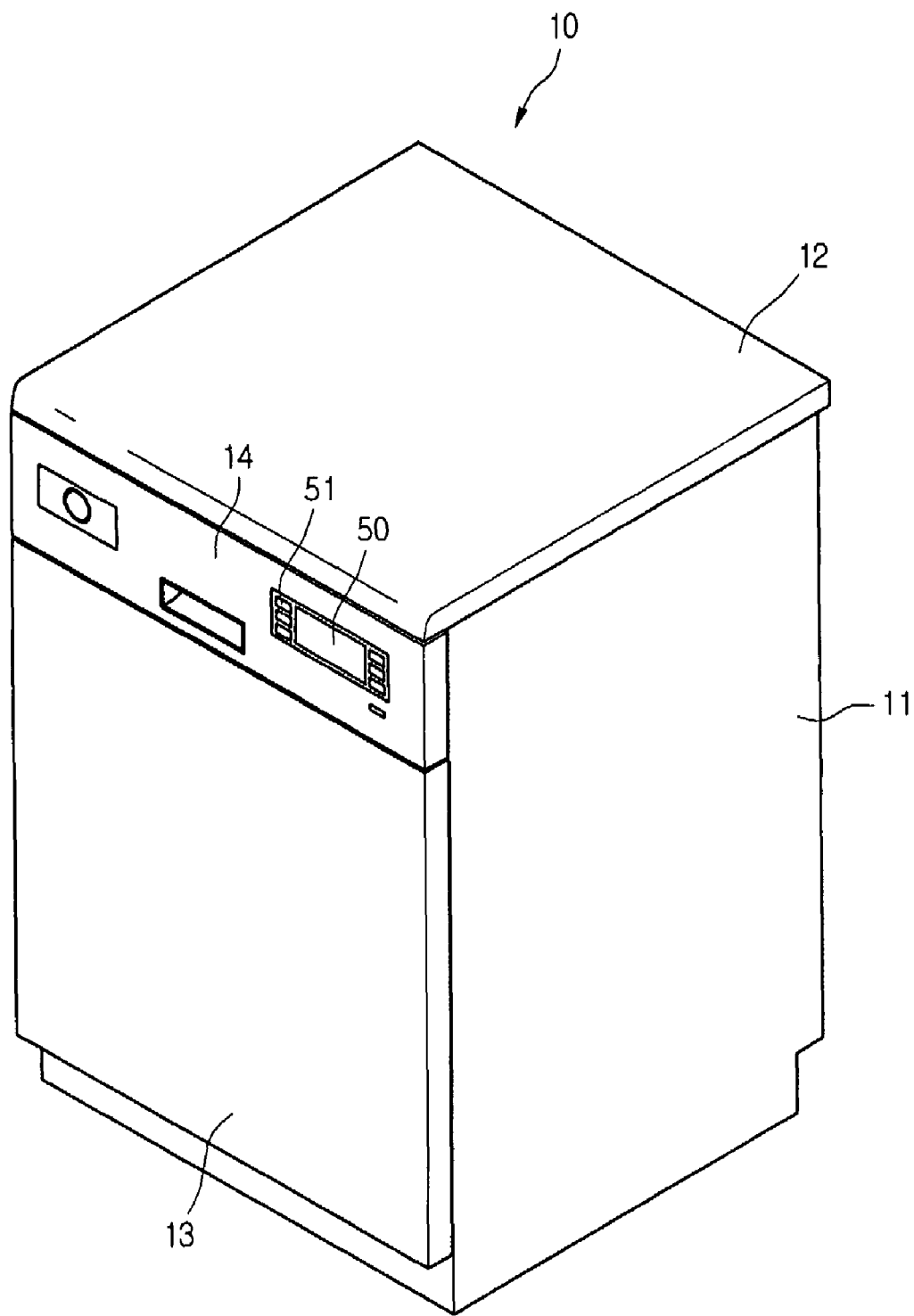
FIG. 1 is a perspective view of a dishwasher with a sterilizer according to the present invention.
Figure 2:
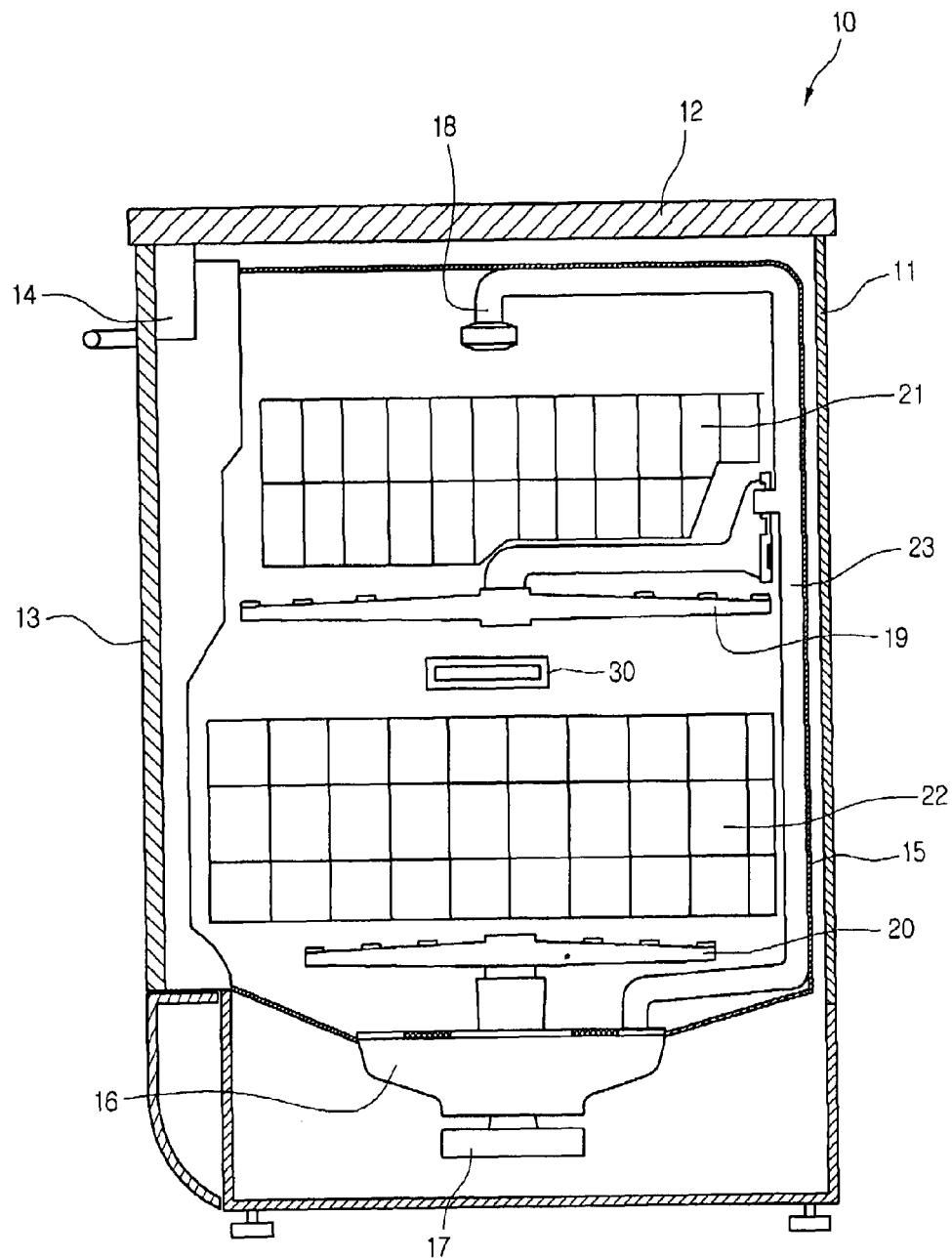
FIG. 2 is a sectional view of the dishwasher in FIG. 1.

FIG. 1 is a perspective view of a dishwasher with a sterilizer according to the present invention, and FIG. 2 is a sectional view of the dishwasher in FIG. 1.

Referring to FIGS. 1 and 2, a dishwasher with a sterilizer includes a cabinet 11 forming an outer shape of the dishwasher, a tub 15 installed inside the cabinet 11 and forming a wash compartment, and a sterilizer 30 installed on an inner wall of the tub 15 to perform sterilizing.

The upper surface of the cabinet 11 has a top cover 12 mounted thereon to form the upper exterior of the dishwasher. Also, a door 13 is installed at the front of the cabinet 11 to pivotably open and close the inside of the dishwasher.

A control panel 14, provided with an input for inputting wash settings, etc. and a display for displaying the duration of a wash course, etc., are installed above the door 13.

The sterilizer 30 may employ an ultraviolet (UV) lamp, a UV light emitting diode (LED), etc. that radiate ultraviolet rays. However, the present invention is not limited thereto, and may alternately employ various devices that emit ultraviolet rays.

Specifically, the front surface of the control panel 14 includes a display 50 that shows the operating state of the dishwasher 10, and a sterilizing button 51 for implementing the sterilizing function is provided at one side of the display 50. Thus, a sterilizing cycle may be added using the sterilizing button 51 to operate independently or in succession with the other cycles.

The dishwasher 10 is installed at the bottom of the tub 15, and includes a sump 16 for storing washing water and spraying members connected to the sump 16 to spray washing water within the tub 15.

Specifically, the spraying members include lower spray arm 20 formed at the floor of the tub 15, an upper spray arm 19 disposed approximately in the center of the tub 15, and a top nozzle 18 installed on the ceiling of the tub 15.

The upper spray arm 19 and the top nozzle 18 are connected to a water guide 23 that extends upward from the top surface of the sump 16. Washing water flows through the water guide 23.

At least one dish rack for storing dishes is provided inside the tub 15. A lower rack 22 may be installed to be capable of being withdrawn at the bottom of the tub 15, and an upper rack 21 may be installed to be capable of being withdrawn at the upper portion of the tub 15.

Also, a wash motor 17 for driving a wash pump and a drain motor (not shown) for driving a drain pump are installed outside the sump 16 to a side thereof.

To briefly describe the operation of the above-configured dishwasher 10, a user first pulls the dish racks 21 and 22 out and places dishes that need to be washed inside, whereupon the user closes the door 13. Then, after the wash settings are inputted and a start button on the front of the door 13 is pressed, washing water flows into the sump 16. When the entry of washing water is completed, the wash motor 17 operates to drive the wash pump.

The washing water pumped by the wash pump is sprayed through the spray nozzle/arms into the tub 15. The high pressure washing water sprayed from the spray nozzle/arms collides with the surfaces of dishes stored on the dish racks 21 and 22 and removes food residue which flows to the floor of the tub 15.

When the wash cycle ends, the contaminated washing water is drained, fresh washing water is admitted, and a rinse cycle commences.

In general, the rinse cycle is performed approximately thrice, with cold water and heated rinsing performed in repetition. The final rinsing is a heated rinsing process, in which a rinse agent is supplied to enable quick removal of moisture from dishes during the drying cycle.

When the rinse cycle is complete, the sterilizer 30 operates during the drying cycle to eradicate bacteria on surfaces of dishes and within the tub.

Below, a detailed description of a sterilizing process performed during the drying cycle will be given with reference to the drawings.

Figure 3:
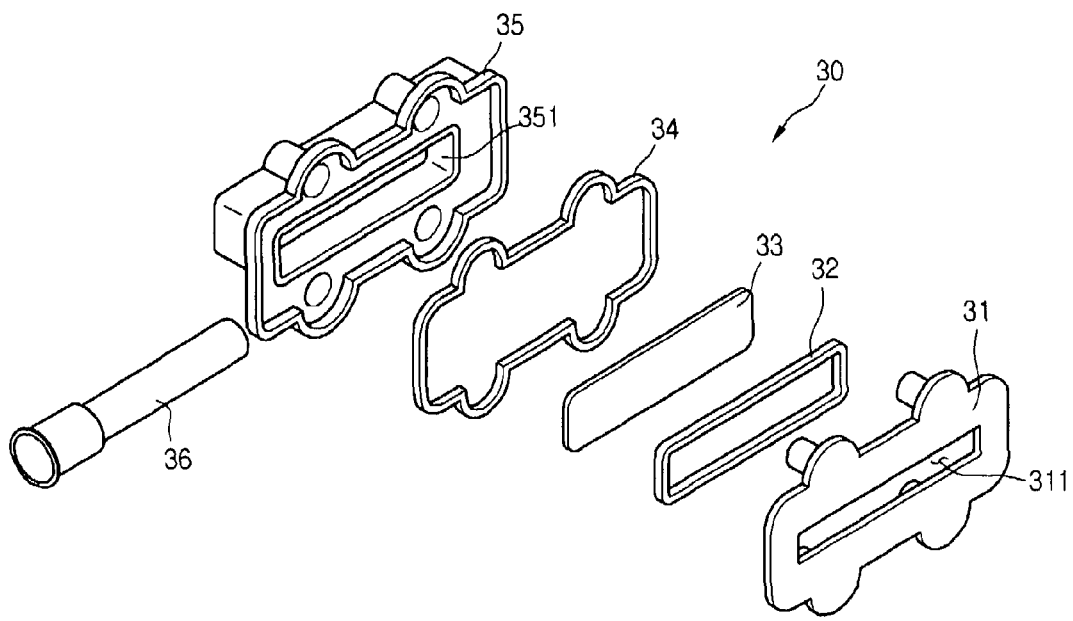
FIG. 3 is an exploded perspective view of a sterilizer according to an embodiment of the present invention.

FIG. 3 is an exploded perspective view of a sterilizer according to an embodiment of the present invention.

Referring to FIG. 3, a sterilizer 30 according to the present invention includes a cover 31, a housing 35 coupled to the rear surface of the cover 31, and a lamp 36 housed inside the housing 35. In detail, the lamp 36 employed may be a UV lamp that emits UV rays, and may be a bulb-type lamp, direct lighting-type lamp, cold cathode lighting-type lamp, etc.

A transmissive opening 311 is provided within the cover 31 to transmit ultraviolet rays emitted from the lamp 36 into the tub 15. Also, a front gasket 32 for preventing washing water from entering the sterilizer is pressed against the perimeter of the transmissive opening 311 at the inner side thereof. A transparent window 33 is installed on the rear surface of the front gasket 32.

The window 33 may be made of a quartz material glass that will not be damaged from ultraviolet rays radiated from the lamp 36 and that can effectively transmit the ultraviolet rays.

A lamp holder 351 for holding the lamp 36 is formed within the housing 35, and the lamp 36 is inserted in the lamp holder 351 from a side of the housing 35. A rear gasket is inserted within the front, outer perimeter of the housing 35, in order to prevent washing water entering the inside of the sterilizer 30.

The sterilizer 30 with the above configuration is installed at one side within the tub. The installed location may be the inner surface of the door, a side of the tub, or the ceiling of the tub. Here, when installing the sterilizer 30 within the tub, the sterilizer 30 may be installed at an optimum location from which the ultraviolet rays from the lamp 36 can be effectively radiated onto the surfaces of dishes.

Figure 4:
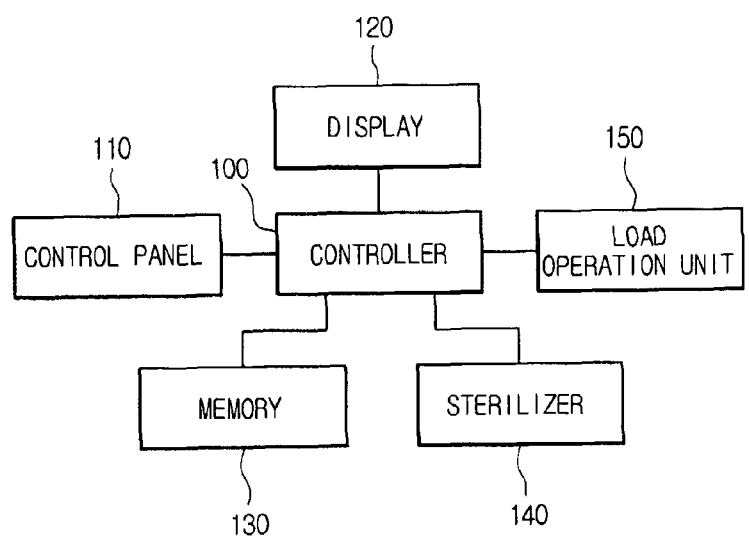
FIG. 4 is a block diagram of a system embodying a sterilizing control method according to the present invention.

FIG. 4 is a block diagram of a system embodying a sterilizing control method according to the present invention.

Referring to FIG. 4, a dishwasher controlling system for performing a sterilizing control method according to the present invention includes a control panel 110, a controller 100, a memory 130, a display 120, a load operation unit 150, and a sterilizer 140.

When wash settings are inputted through the control panel 110, the controller 100 controls the operation of the system according to the inputted commands.

The memory 130 stores the commands inputted through the control panel 110 and various other data. Also, the display 120 displays the status of system operation performed by the controller 100.

The load operation unit 150 is connected to the controller 100, and operates the various driving devices according to the commands inputted through the control panel 110.

The sterilizer 140 operates when the sterilizing cycle is selected through the control panel 110 during the drying cycle.

Specifically, the load operation unit 150 includes wash and drain pumps, a heater, etc., and the sterilizer 140 includes the sterilizer 30 shown in FIG. 2 (which can be a UV lamp).

In the above-configured system, the controller 100 receives wash selections inputted through the control panel 110, and the selections are stored in the memory 130.

Then, the controller 100 calculates the duration of the entire wash course and the remaining time in accordance with the inputted commands, and sends the calculated data to the display 120. The display 120 then displays the data according to the inputted selections.

Next, the operating commands are sent from the controller 100 to the load operation unit 150 to operate the various devices.

Then, the sterilizer 140 is activated when the drying cycle is begun, removing bacteria inside the tub. Here, the sterilizer 140 is repeatedly turned on and off at predetermined intervals by the controller 100.

Specifically, the sterilizer 140 is turned on for a predetermined duration to perform sterilizing, and the sterilizer 140 is turned off for a predetermined duration.

Also, the drying fan does not operate while the sterilizer 140 operates. Only when the sterilizer 140 does not operate is the drying fan operated to discharge moist air to the outside of the dishwasher.

Figure 5:
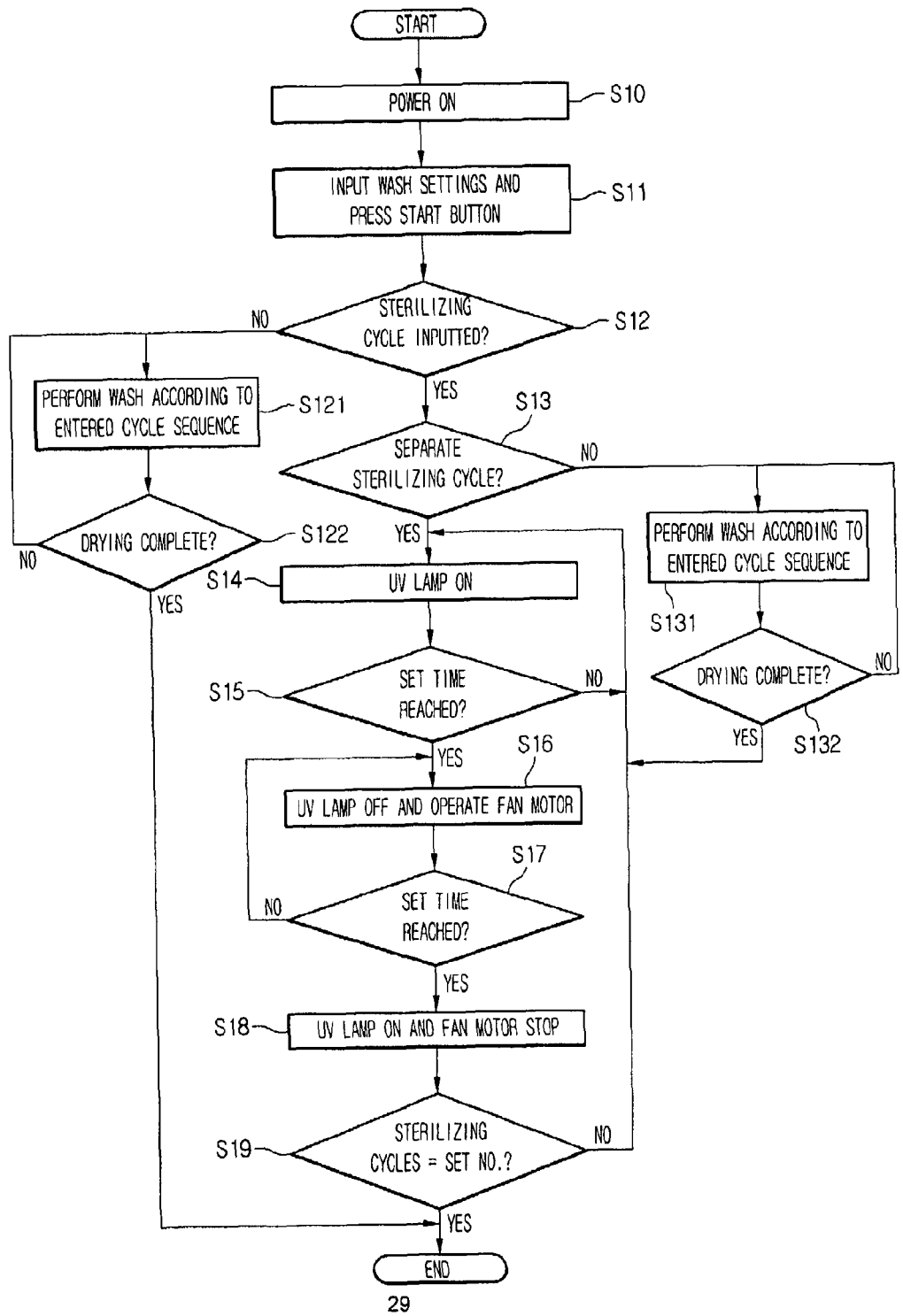
FIG. 5 is a flowchart of a sterilizing control method for a dishwasher according to the present invention.

FIG. 5 is a flowchart of a sterilizing control method for a dishwasher according to the present invention.

Referring to FIG. 5, a sterilizing cycle according to the present invention may be performed separately or together with other cycles of a wash course.

In detail, a user first presses a power button to apply power to the dishwasher in step S10, and enters wash selections using input buttons. When the entering of wash selections is completed, an activation command is entered through pressing a start button in step S11.

When the operating commands are inputted, the controller 100 deciphers the inputted command data and determines whether a sterilizing cycle has been entered in step S12. That is, when it is determined that a sterilizing cycle has been selected, the controller 100 determines in step S13 whether the sterilizing cycle that was inputted is to be performed separately or together with the other cycles of the wash course.

Furthermore, when it is determined that the inputted sterilizing cycle is to be separately performed, the sterilizer (a UV lamp, for instance) is turned on to radiate ultraviolet rays in step S14. The 'on' state of the UV lamp is sustained for a set duration, during which the controller 100 determines in step S15 whether the set duration has been elapsed. When it is determined that the set duration has elapsed, the UV lamp is turned off and the fan motor is activated in step S16.

That is, the drying fan rotates to exhaust the moist vapor from inside the tub to the outside. Here, the UV lamp may be maintained in an 'on' state for 20 minutes. Should the 'on' state be maintained for less than 20 minutes, there is the possibility that bacteria may not be eradicated. Thus, even when a sterilizing process has been performed, bacteria may still remain in the tub.

The controller also determines in step S17 whether the operating duration of the fan motor has reached a set time, and when the set time is reached, the UV lamp is turned back on and the fan motor is turned off in step S18.

In order to allot ample time for sterilizing, the operating time of the sterilizer may be longer than the operating time of the drying fan.

It is determined in step S19 whether the number of times that the UV lamp is turned on (or the number of sterilizing cycles) reaches a set number. When it is determined that the number of sterilizing cycles reaches the set number, the sterilizing cycles are ended. When it is determined that the set number has not been reached, the UV lamp is continuously turned on and off to repeat sterilizing.

When the controller determines that a sterilizing cycle was not inputted, in step S121, the wash course is performed in the order of cycles specified by the inputted wash settings. In other words, the wash, rinse, and drying cycles are performed sequentially. In step S122, it is determined if the drying cycle has been completed, and when the drying is determined to have been completed, the entire wash course is ended.

In the case where a sterilizing cycle is inputted as an option to be added to the wash course, the wash course is performed in step S131 according to the inputted sequence of cycles. The controller determines in step S132 whether the drying cycle has been completed. The controller determines in step S132 whether the drying cycle is completed. At the same time that the drying cycle is being completed, the sterilizing cycle is performed. In other words, when the drying cycle is completed, the UV lamp is turned on and off at regular intervals, operating alternately with the drying fan.

In the above configuration, the sterilizing cycle may be performed alone or added as an option to a wash course, so that the sterilizer is repeatedly turned on and off at regular intervals.

The sterilizing control method of a dishwasher according to the present invention has the advantage eradiating pathogenic bacteria such as salmonella, vibrio, and bacillus subtilis from the tub.

Also, by regularly and repeatedly performing sterilizing cycles at predetermined intervals, the sustaining and re-growth of bacteria can be prevented at the source.

Therefore, by eradicating germs to prevent re-growth thereof, the inside of a dishwasher can always be maintained in a hygienic state.

It will be apparent to those skilled in the art that various modifications and variations can be made in the present invention. Thus, it is intended that the present invention covers the modifications and variations of this invention provided they come within the scope of the appended claims and their equivalents.

What is claimed is:

1. A sterilizing control method for a dishwasher, comprising:
    inputting wash preferences for a sterilizing cycle through a control panel;
    determining whether the inputted wash preferences are for performing a stand-alone sterilizing cycle or adding a sterilizing cycle as an option with other cycles of a wash course, the other cycles including at least one of a wash cycle, a rinse cycle and a drying cycle; and
    performing the sterilizing cycle without a wash cycle and a rinse cycle when the stand-alone sterilizing cycle is selected, and performing the sterilizing cycle after the other cycles are completed when the sterilizing cycle is added as an option with other cycles of a wash course,
    wherein performing the sterilizing cycle comprises:
        turning a sterilizer on and off at regular intervals; and
        operating a drying fan to exhaust moist vapor to outside of the dishwasher while the sterilizer is turned off, and
    wherein when the sterilizer is turned on, the drying fan ceases operating, and when the sterilizer is turned off, the drying fan operates.

2. The sterilizing control method according to claim 1, wherein the sterilizer comprises an ultraviolet lamp or an ultraviolet light emitting diode, for radiating ultraviolet rays.

3. The sterilizing control method according to claim 1, wherein, when the stand alone sterilizing cycle is selected, an operating duration of the sterilizer is longer than an operating duration of the drying fan.

4. The sterilizing control method according to claim 1, wherein the inputting of the command for the sterilizing cycle comprises setting a number of on/off loops of the sterilizer.

5. The sterilizing control method according to claim 1, wherein the inputting of the command for the sterilizing cycle comprises setting an operating time of the sterilizer.

6. The sterilizing control method according to claim 1, wherein an operating duration of the sterilizer is at least 20 minutes.

\* \* \* \* \*